United States Patent [19]

Perry et al.

[11] 3,966,834

[45] June 29, 1976

[54] PROCESS FOR THE SEPARATION OF DIENE FROM ORGANIC MIXTURES

[75] Inventors: Eli Perry, St. Louis; William F. Strazik, St. Ann, both of Mo.

[73] Assignee: Monsanto Company, St. Louis, Mo.

[22] Filed: Sept. 22, 1972

[21] Appl. No.: 291,453

[52] U.S. Cl. ............... 260/681.5 R; 260/677 A; 208/291; 208/308
[51] Int. Cl.² ............................................. C07C 7/00
[58] Field of Search ............... 260/681,5, 677 A; 208/308, 291

[56] References Cited
UNITED STATES PATENTS

| 2,947,687 | 8/1960 | Lee .................................. 208/308 |
| 2,953,502 | 9/1960 | Binning et al. ..................... 203/14 |
| 2,960,462 | 11/1960 | Lee et al. ........................... 208/308 |
| 3,062,905 | 11/1962 | Jennings et al. ................... 260/677 A |
| 3,370,102 | 2/1968 | Carpenter et al. ................. 208/308 |
| 3,819,742 | 6/1974 | Brun et al. ......................... 260/681.5 R |

FOREIGN PATENTS OR APPLICATIONS

| 2,112,632 | 6/1972 | France ............................. 260/681.5 |

*Primary Examiner*—Delbert E. Gantz
*Assistant Examiner*—Veronica O'Keefe

[57] ABSTRACT

Dienes are separated from organic mixtures comprising diene and alkene having one double bond by contacting the mixture against one side of a membrane which is a halogenated polymer of ethylene and withdrawing at the other side a vaporous mixture having increased diene concentration. Exemplary of the organic mixtures is a mixture of butadiene and butene. Exemplary of the membranes are polyvinylchloride and tetrafluoroethylene/ethylene copolymer.

8 Claims, No Drawings

PROCESS FOR THE SEPARATION OF DIENE FROM ORGANIC MIXTURES

BACKGROUND OF THE INVENTION

1. Field of the Invention

This invention relates to a process for separating dienes from organic mixtures containing same. In a particular aspect this invention relates to a process for the separation of diene from organic mixtures comprising diene and alkene having one double bond by preferential permeation through a membrane under pervaporation conditions. In a more particular aspect this invention relates to a process for the separation of diene from an organic mixture comprising diene and alkene having one double bond by contacting said mixture against one side of a polymeric membrane which is a halogenated polymer of ethylene and recovering on the other side a vaporous mixture rich in diene.

2. Description of the Prior Art

Processes for the preparation of dienes such as butadiene and isoprene yield reaction mixtures which contain organic reaction products (typically substituted and unsubstituted $C_3$–$C_{12}$ hydrocarbons) in addition to organic solvents and the desired diene. Separation of dienes from such organic reaction media has been accomplished by distillation procedures. Principally because of the close boiling points of dienes and typical reaction by-products, especially the corresponding alkenes having one double bond high reflux ratios or azeotropic agents and costly distillation equipment are required for the distillation separation procedure.

Separation of components of azeotropic mixtures of organic materials by pervaporation through polymer membranes is known to the art from U.S. Pat. No. 2,953,502 issued Sept. 20, 1960 to R. C. Binning and Robert J. Lee.

SUMMARY OF THE INVENTION

It has been discovered in accordance with the present invention that dienes are effectively separated from organic mixtures comprising diene and alkene having one double bond by contacting the mixture against one side of a membrane which is a halogenated polymer of ethylene and withdrawing at the second side a vaporous mixture having a higher concentration of diene than the aforesaid mixture. The vinyl polymer membranes employed in the process of the present invention are highly efficient in separating diene from other components of such organic mixtures using pervaporation separation techniques. The present invention is further advantageous in that it permits avoidance of costly distillation procedures.

DETAILED DESCRIPTION

The process of the present invention comprises contacting an organic feed mixture comprising diene and alkene having one double bond against one side of a membrane which is a halogenated polymer of ethylene and withdrawing at the second side a mixture having a higher concentration of the preferentially permeable diene than the aforesaid feed mixture. It is essential that the mixture at the second side be maintained at a lower chemical potential than that on the feed side. It is also essential that the product be withdrawn at the second side in the vapor state. In the commercial utilization of the process, mullti-stage operation is feasible since this permits the operation of individual stages at various concentrations and temperatures in order to achieve the optimum driving force for the process.

For each individual stage the effectiveness of the separation is shown by the separation factor (S.F.).

The separation factor (S.F.) is defined as the ratio of the concentrations of two substances, A and B, to be separated divided into the ratio of the concentrations of the corresponding substances in the permeate, $$S.F. = \frac{(C_A/C_B) \text{ in permeate}}{(C_A/C_B) \text{ in permeant}}$$

where $C_A$ and $C_B$ are the concentrations of the preferentially permeable component and any other component of the mixture or of the sum of other components respectively.

In carrying the process of the present invention, the first or feed side of the membrane is such that the activities of the components are greater than the activities on the second side. Preferably the first side is above atmospheric pressure and the second side below atmospheric pressure. Still more preferably, the second side is maintained such that the pressure differential is greater than 0.01 atmosphere or preferably from about 0.1 to about 0.5 atmosphere. A further preferred mode of operation is with the second side maintained at a vacuum of greater than 0.2 mm. Hg.

The term "Chemical Potential" is employed herein as described by Olaf A. Hougen and K. M. Watson ("Chemical Process Principles, Part II", John Wiley, New York, 1947). It is related to the escaping tendency of a substance from any particular phase. For an ideal vapor or gas, this escaping tendency is equal to the partial pressure so that it varies greatly with changes in the total pressure. For a liquid, the change in escaping tendency as a function of total pressure is small. The escaping tendency always depends upon the temperature and concentration. In the present invention, the feed substance is typically a liquid solution and the other side of the membrane is maintained such that a vapor phase exists. A vapor feed may be employed when the mixture to be separated is available in that form from an industrial process or when heat economies are to be effected in a multi-stage process.

The feed side may be at pressures less than atmospheric, but preferably greater than atmospheric and also at pressures over and above the vapor pressure of the liquid components. The collection or permeate vapor side of the membrane is preferably less than atmospheric pressure, but under proper feed side conditions, also may be greater than atmospheric pressure. The total pressure on the feed side is preferably between 0 psi absolute and 5000 psig.

The conditions are always such as to maintain a higher chemical potential on the feed side than on the collection or vapor side.

The temperatures on the feed side and the collection side may vary over a wide range. However, temperatures should be avoided which cause substantial decomposition of any of the organic materials in the mixture or of the membrane and which cause the vapor pressure on the collection side of any of the permeated materials to be exceeded by the pressure being maintained on that side. Typically, an increase in temperature causes an increase in permeation rate. A dramatic increase in rate often occurs when the temperature exceeds the glass transition temperature of the polymer membrane being used in the separation procedure.

The process of the present invention provides for the separation of diene from organic mixtures comprising diene and alkene having one double bond. Such dienes are substituted and unsubstituted and typically contain from 4 to 8 carbon atoms. A diene may be substituted with, for example alkyl, aromatic and halogen substituents. Typical organic components and mixtures from which the dienes are separated include $C_3 - C_{12}$ alkenes such as butene, hexene, propylene, and heptene as well as other hydrocarbons such as chlorohexane, acrylic acid, octane, propane, etc. and the like. Separations are carried out by removal of the preferentially permeable diene through the membrane with the said diene, in a higher concentration than in the feed, being recovered from the collection side of the membrane as a vapor and with the imposition of a state of lower chemical potential on such collection side of the membrane. For example, a mixture of butadiene and butene may be applied to one side of a flat diaphram or membrane to accomplish removal of at least a part of the butadiene, leaving a more highly concentrated butene solution at the feed side of the membrane or diaphram. A state of lower chemical potential is maintained on the collection or downstream side of the membrane by vacuum e.g. from 0.1 mm Hg. to the vapor pressure of the organic component of the mixture which has the lowest vapor pressure at the membrane at the respective temperature as long as the vapor phase is present on the downstream side.

In the system referred to above, the butadiene selectively passes through the membrane with the butadiene-rich composition being rapidly removed as vapor from the collection side of the membrane.

In contrast to the present invention, the employment of permeates in liquid phase or the second side of the membrane is impractical because the applied pressure has been found to be prohibitively high, e.g. up to 1,000 atmospheres being necessary because of osmotic pressures. Liquid-liquid permeation is largely an equilibrium phenomenon unless the osmotic forces are overcome while in contrast liquid-vapor or vapor-vapor permeations are rate controlled processes even at moderate conditions, in which the vapor is removed as soon as it reaches the collection surface of the membrane. Liquid-vapor and vapor-vapor separations are accordingly much more effectively carried out than liquid-liquid separations.

The permeation membrane used in the process of the present invention comprises halogenated vinyl polymers of ethylene. The polymer can be a homopolymer, a copolymer or a polymer blend. When the halogenated vinyl polymer is a polymer blend or a copolymer of the vinyl polymer and another monomer copolymerizable therewith, the copolymer or blend should contain a sufficient amount of the halogenated vinyl polymer to substantially maintain the physical and chemical characteristics of that materials. The essential halogenated vinyl polymer typically constitutes 50% or more of the total polymeric material. In the case of copolymers the percentage is mole percent and in the case of blends the percentage is weight percent. For functional purposes copolymers in which the halogenated vinyl polymer constitutes more than 97% of the total polymeric material are considered to be homopolymers. Examples of halogenated polymers of ethylene suitable as membranes in the process of the present invention include poly(vinylchloride), poly(vinylfluoride), poly(vinylidenefluoride), poly(vinylidenechloride), copolymer of vinyl chloride and ethylene, copolymer of vinyl chloride and vinyl acetate, copolymer of tetrafluoroethylene and ethylene etc. and the like.

The membrane may be a simple disc or sheet of the membrane substance which is suitably mounted in a duct or pipe, or mounted in a plate and frame filter press. Other forms of membranes may also be employed such as hollow tubes and fibers through which or around which the feed is supplied or is recirculated with the product being removed at the other side of the tubes as a vapor. Various others shapes and sizes are readily adaptable to commercial installations. The membrane, of course, must be insoluble in the organic separation medium. "Membrane insolubility" as used herein is taken to include that the membrane material is not substantially solution-swellable or sufficiently weakened by its presence in the solution to impart "rubbery" characteristics which can cause creep and rupture under the conditions of use, including high pressures. The molecular weight of the polymer may vary over a wide range, but in all cases should be sufficient to permit the polymer to be formed into a film which is sufficiently strong to withstand separation processing conditions.

The membranes may be prepared by any suitable procedure such as, for example, by casting a film or spinning a hollow fiber from a "dope" containing polymer and solvent. Such preparations are well known to the art.

An important control over the separation capacity of a particular membrane is exercised by the method used to form and solidify the membrane (e.g. casting from a melt into controlled atmospheres or from solution into baths at various concentrations and temperatures).

The art of membrane usage is well known with substantial literature being available on membrane support, fluid flow and the like. The present invention is practiced with such conventional procedures and apparatus. The membrane must, of course, be sufficiently thin to permit permeation as desired, but sufficiently thick so as to not rupture under the pressure conditions employed. Typically suitable membranes have a thickness of from about ½ to about 10 mils.

The following examples illustrate specific embodiments of the present invention. In the examples the membranes employed were in the form of film disks and were mounted in a membrane holder. All membranes were prepared by casting from solution.

EXAMPLE 1

Membrane permeations were conducted for the purpose of separating 1,3-butadiene from an organic liquid consisting of 80 weight percent 1,3-butadiene and 20 weight percent tran-2-butene using membranes which are halogenated polymers of ethylene. Each membrane was approximately 1 mil in thickness. In each run, the pressure on the liquid side was higher than the pressure on the vapor side and was that pressure caused by the vapor pressure of the mixture at the temperature of separation. The results are shown in the Table.

EXAMPLE 2

The procedure of Example 1 is followed to separate isoprene from a liquid mixture of isoprene, hexene, and pentane using a poly(vinylchloride) membrane.

The halogenated polymers of ethylene as named herein refer to the molecular structure of the polymers and are not limited to polymers prepared by the polymerization of the corresponding monomer.

While the invention has been described with reference to particular embodiments thereof, it will be appreciated that modifications and variations are possible without departing from the invention.

TABLE

| Run No. | Polymer Membrane | *Permeation Rate × 10⁴ | Separation Factor (SF) |
|---------|------------------|------------------------|------------------------|
| 1 | poly(vinylchloride) | 1200 | 2.2 |
| 2 | poly(vinyl fluoride) | 2.8 | 2.9 |
| 3 | poly(vinylidene fluoride) | 0.8 | 3.1 |
| 4 | copolymer[tetrafluoroethylene/ethylene (45%)] | 150 | 1.9 |
| 5 | copolymer[vinylchloride/ethylene (20%)] | 2500 | 2.4 |
| 6 | copolymer[vinylchloride/vinylacetate (13%)] | 740 | 2.83 |

*Grams per hour per 11.3 cm² per mil of membrane thickness

We claim:

1. A process for separating dienes from an organic mixture comprising dienes having from 4 to 8 carbon atoms per molecule and alkenes having one double bond and from 3 to 12 carbon atoms per molecule which comprises:

contacting the mixture against a first side of a membrane which is selected from the group consisting of poly (vinyl chloride), poly (vinyl fluoride), poly (vinylidene fluoride), tetrafluoroethylene/ethylene copolymer, vinyl chloride/ethylene copolymer, and vinylchloride/vinylacetate copolymer; and withdrawing from a second side of the membrane a vaporous mixture having a higher concentration of dienes than the aforesaid organic mixture with the mixture at the second side being maintained at a lower chemical potential than the mixture on the first side of the membrane.

2. The process of claim 1 wherein the pressure on the second side of the membrane is less than atmospheric pressure and lower than the pressure on the first side of the membrane.

3. A process for separating butadiene from an organic mixture comprising butadiene and trans-2-butene which comprises:

contacting the mixture against a first side of a poly(-vinyl chloride) membrane; and withdrawing from a second side of the membrane a vaporous mixture having a higher concentration of butadiene than the aforesaid organic mixture with the mixture at the second side being maintained at a lower chemical potential than the mixture on the first side of the membrane.

4. A process for separating butadiene from an organic mixture comprising butadiene and trans-2-butene which comprises:

contacting the mixture against a first side of a poly(-vinyl fluoride) membrane; and withdrawing from a second side of the membrane a vaporous mixture having a higher concentration of butadiene than the aforesaid organic mixture with the mixture at the second side being maintained at a lower chemical potential than the mixture on the first side of the membrane.

5. A process for separating butadiene from an organic mixture comprising butadiene and trans-2-butene which comprises:

contacting the mixture against a first side of a poly (vinylidene fluoride) membrane; and withdrawing from a second side of the membrane a vaporous mixture having a higher concentration of butadiene than the aforesaid organic mixture with the mixture at the second side being maintained at a lower chemical potential than the mixture on the first side of the membrane.

6. A process for separating butadiene from an organic mixture comprising butadiene and trans-2-butene which comprises:

contacting the mixture against a first side of a tetrafluoroethylene/ethylene copolymer membrane; and withdrawing from a second side of the membrane a vaporous mixture having a higher concentration of butadiene than the aforesaid organic mixture with the mixture at the second side being maintained at a lower chemical potential than the mixture on the first side of the membrane.

7. A process for separating butadiene from an organic mixture comprising butadiene and trans-2-butene which comprises:

contacting the mixture against a first side of a vinylchloride/ethylene copolymer membrane; and withdrawing from a second side of the membrane a vaporous mixture having a higher concentration of butadiene than the aforesaid organic mixture with the mixture at the second side being maintained at a lower chemical potential than the mixture on the first side of the membrane.

8. A process for separating butadiene from an organic mixture comprising butadiene and trans-2-butene which comprises:

contacting the mixture against a first side of a vinylchloride/vinylacetate copolymer membrane; and withdrawing from a second side of the membrane a vaporous mixture having a higher concentration of butadiene than the aforesaid organic mixture with the mixture at the second side being maintained at a lower chemical potential than the mixture on the first side of the membrane.

* * * * *